(12) United States Patent
Fuisz et al.

(10) Patent No.: US 11,064,907 B2
(45) Date of Patent: *Jul. 20, 2021

(54) METHOD AND SYSTEM TO AMPLIFY AND MEASURE BREATH ANALYTES

(71) Applicants: Richard C. Fuisz, Bay Harbor, FL (US); Joseph M. Fuisz, Surfside, FL (US)

(72) Inventors: Richard C. Fuisz, Bay Harbor, FL (US); Joseph M. Fuisz, Surfside, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/709,494

(22) Filed: Sep. 20, 2017

(65) Prior Publication Data

US 2018/0008167 A1    Jan. 11, 2018

Related U.S. Application Data

(63) Continuation of application No. 13/423,527, filed on Mar. 19, 2012, now Pat. No. 9,770,192.

(51) Int. Cl.
*A61B 5/097*    (2006.01)
*A61B 5/08*    (2006.01)
*G01N 33/497*    (2006.01)

(52) U.S. Cl.
CPC .............. *A61B 5/097* (2013.01); *A61B 5/082* (2013.01); *G01N 33/497* (2013.01)

(58) Field of Classification Search
None
See application file for complete search history.

(56) References Cited

U.S. PATENT DOCUMENTS

| 5,971,937 A | 10/1999 | Elstrom |
| 6,718,980 B2 | 4/2004 | Carter |
| 7,364,553 B2 | 4/2008 | Paz et al. |
| 2004/0096401 A1 | 5/2004 | Patton et al. |
| 2006/0257463 A1 | 11/2006 | Elsohly |
| 2010/0137733 A1 | 6/2010 | Wang |

(Continued)

OTHER PUBLICATIONS http://www-personal.umich.edu/~lpt/oxlabel.htm; Oxygen: Concentrations, Grades, and Labels (Year: 2008).*

(Continued)

*Primary Examiner* — Kaylee R Wilson
*Assistant Examiner* — Jay B Shah
(74) *Attorney, Agent, or Firm* — Fitch, Even, Tabin & Flannery, LLP

(57) ABSTRACT

A method of avoiding a contaminant which would skew an analyte result in a breath analysis method and of calibrating subject of the breath analysis includes, immediately before the breath analysis method or the collection of breath for the breath analysis method, administering to the subject a predetermined gas composition. A system for analyzing an analyte in breath of a subject while avoiding a local contaminant which would skew an analyte result and calibrating the subject of so that the result of the analyte analysis will be the same regardless of where the test is performed geographically, includes a source of a predetermined gas composition immediately before the breath analysis method or the collection of gas for the breath analysis method, administering to the subject a predetermined gas mixture.

2 Claims, 5 Drawing Sheets

(56) References Cited

U.S. PATENT DOCUMENTS

Figure 1:
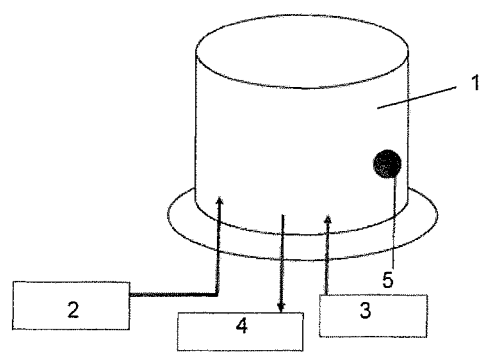

| | | | |
|---|---|---|---|
| 2010/0147302 A1* | 6/2010 | Selvarajan | A61M 16/00 128/204.23 |
| 2011/0098589 A1 | 4/2011 | Clemensen | |
| 2011/0201958 A1* | 8/2011 | Lazar | A61B 5/097 600/538 |
| 2013/0190640 A1* | 7/2013 | Adam | A61B 5/087 600/538 |

OTHER PUBLICATIONS http://files.shareholder.com/downloads/OPKO/1605280361x0x518628/c74bb6cb-fcfb-4340-9c37-f6db9f4fd088/OPKO-Lazard-Presentation-Nov-11-2011_Final.pdf.
http://www.globalpost.com/dispatch/news/regions/americas/united-states/110818/dogs-smell-lung-cancer-study.
http://en.wikipedia.org/wiki/Canine_cancer_detection.
Galassetti, "A Breath Test for Blood Glucose" published The Healthy Living Magazine's Diabetes Forecast Jan. 2010 describing Prof. Galassetti's work.
International Search Report/Written Opinion, PCT/US2013/029005, Apr. 25, 2013.
Restrepo et al., Humidification during Invasive and noninvasive mechanical ventilation: 2012, vol. 57(5), p. 782-788, May 2012.

* cited by examiner

METHOD AND SYSTEM TO AMPLIFY AND MEASURE BREATH ANALYTES

CROSS-REFERENCE TO RELATED APPLICATION

This application is a continuation of application Ser. No. 13/423,527, filed Mar. 19, 2012.

BACKGROUND OF THE INVENTION

Medical Progress has followed a common thematic trend line in favor of less invasive diagnosis and treatment.

For example, surgeons have dramatically expanded the range of procedures through laparoscopy. The use of such procedures frequently reduces patient recovery time, otherwise improve surgical results, and perhaps most importantly make it more likely that patients will actually seek out corrective measures.

Similarly, laser therapies are employed to remedy various conditions.

In the field of diagnostics, magnetic image resonance and other scanning methods are routinely used for non-invasive real time diagnosis of the body of humans and animals.

In drug development, too we see this same trend. Drug therapies are developed to replace surgical resolution where possible. And, innovators seek less invasive drug delivery methods. For example, Revance Therapeutics is hard at work on a topically administered Botox to possibly enable Botox users to avoid the discomfort of injection. Oral insulin is the Holy Grail for would-be drug delivery innovators.

The field of blood analyzers, including personal analyzers, has advanced. Much of this innovation has been enabled by the proliferation of personal analyte monitors with attendant advances in the use of methods to minimize the discomfort associated with blood sampling. Still, even with these examples such sampling is not a preferred activity except for the convenience thereby offered by personal testing as compared with lab-based testing.

Advances in microfluidics testing allows for real time (or near real time) testing of various bodily fluids. For example, Opko health's system can test (or potentially test) blood, saliva, semen, spinal fluid, serum, tears, urine, amniotic fluid or sweat. See, http://files.shareholder.com/downloads/OPKO11605280361x0x518628/c74bb6cb-fcfb-4340-9c37-f6db9f4fd088/OPKO-Lazard-Presentation-Nov-11-2011_Final.pdf.

When one considers the area of less invasive diagnostics, the use of the breath is an area that will be in our future. It has been demonstrated, for example, that some animals, like dogs, are able to detect the presence of cancer in the breath of cancer patients to high level of accuracy. Such detection is thought to rely upon the olfactory ability of dogs to detect very low concentrations of the alkanes and aromatic compounds generated by tumors (see http://www.globalpost-.com/dispatch/news/regions/americas/united-states/110818/dogs-smell-lung-cancer-study; see also http://en.wikipedia.org/wiki/Canine_cancer_detection).

Xhale, a Florida-based company (www.xhale.com), is working to develop a breath based-glucose monitoring system for use in connection with the treatment of diabetes and other applications. Similarly, Prof. Pietro Galassetti, at University of California at Irvine, is reportedly at work on a system to monitor glucose levels in breath (see "A Breath Test for Blood Glucose" published The Healthy Living Magazine's Diabetes Forecast January 2010 describing Prof. Galassetti's work).

However, the trend towards less invasive diagnostic methods—including methodologies based on breath—will be in our near future. As in any area, there are challenges along the way for innovators and inventors to solve. A review of the prior art in breath-based diagnostics reveals a number of challenges. Indeed, the absence of breath diagnostics from the commercial space—apart from law enforcement use of the breathalyzer—demonstrates that such challenges have not yet been surmounted by the state of the art. Thus, further invention is required to develop the field of breath diagnostics.

SUMMARY OF THE INVENTION

The present invention relates, inter alia, to a method of avoiding a contaminant which would skew an analyte result in a breath analysis method and of calibrating the subject of the breath analysis including, immediately before the breath analysis method and/or the collection of breath for the breath analysis method, administering to the subject a predetermined gas composition.

The breath analysis may then be conducted immediately on the subject. Alternatively, immediately after the predetermined period of time, a plurality of exhaled breaths of the subject may be collected in a closed container, and the breath analysis conducted on the plurality of exhaled breaths collected in the closed container. In one embodiment of the invention, the closed container is expandable.

In one embodiment of the invention, the predetermined gas composition is a purified and standardized gas mixture.

In an embodiment of the invention, the step of administering to the subject the predetermined gas composition includes having the subject inhale the predetermined gas mixture from a source of the predetermined gas mixture, and exhale outside the source of the predetermined gas mixture for a predetermined period of time, in order to calibrate the subject and eliminate through washout and non repeat inhalation the majority of ambient analyte contaminants, so that analytical results can be reasonably attributed to the individual subject.

In one embodiment of the invention, the predetermined period of time is at least 350 seconds. In another embodiment of the invention, the predetermined period of time is at least 300 seconds. In another embodiment of the invention, the predetermined period of time is at least 250 seconds.

In one embodiment of the invention, the predetermined gas composition comprises bone dry calibration air.

In one embodiment of the invention, the predetermined gas composition further includes a bronchodilator to augment and amplify the potential for transfer of analyte from blood to breath.

In one embodiment of the invention, the predetermined gas composition can also include an amplification agent to facilitate the transfer of the analyte from the blood to the breath and may be used in the washout and/or in the test period.

The present invention also relates to, inter alia, a system for analyzing an analyte in breath of a subject while avoiding a local contaminant which would skew an analyte result and calibrating the subject of so that the result of the analyte analysis will be the same regardless of where the test is performed geographically, comprising a source of a predetermined gas composition immediately before the breath analysis method or the collection of gas for the breath analysis method, administering to the subject a predetermined gas mixture.

BRIEF DESCRIPTION OF THE DRAWING FIGURES

FIG. 1 schematically shows the experimental setup for the examples.

Figure 2:
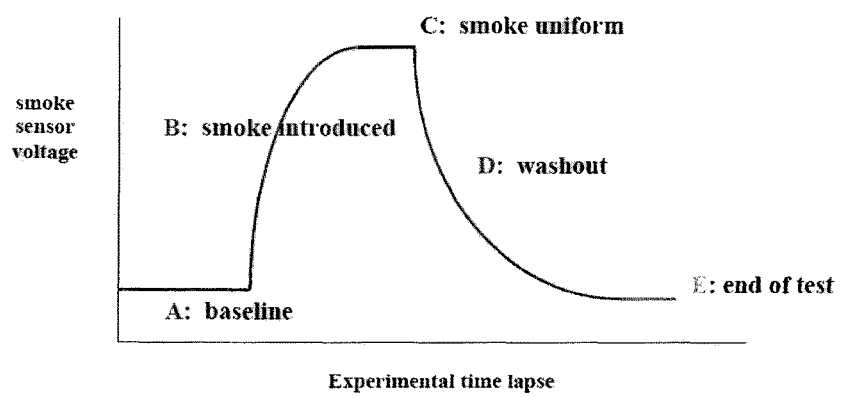

FIG. 2 conceptually illustrates the steps and results "A" through "E" of the examples.

FIGS. 3-7 show experimental results.

DISCLOSURE OF THE INVENTION

In large part the use of the breath as a diagnostic tool will be increasingly aided by the various techniques which are evolving using but not limited to an evolution of the computer chip allowing for the detection of smaller and smaller amounts of analyte. As this is occurring it becomes more and more apparent that in the future a visit to a health care provider may well involve a breath examination instead of or in addition to blood analysis. Personal breath analyzers will also come to pass. One must keep in mind that both blood and breath are in fact fluids. As will be seen from this disclosure, they involve differing challenges however.

Breath is a unique bodily fluid. Unlike blood and others, it is available on a breath-to-breath and thus on a continuous basis. It is readily available for sampling non-invasively and because the lung receives the blood flow from the right heart, measurements of analytes in breath can correlate strongly with blood presence and/or concentration.

Average respiratory rate reported in a healthy adult at rest is usually given as 12-18 breaths per minute (Vf) but estimates do vary between sources, e.g., 12-20 breaths per minute, 10-14, between 16-18, etc. With such a slow rate, more accurate readings are obtained by counting the number of breaths over a full minute.

Average total lung capacity for a healthy male is six liters; for women the figure is 4.2 liters.

Exhaled breath contains up to 100% humidity at 37° C. (normal body temperature) and thus can often be considered an aerosol.

Notwithstanding the obvious benefits of breath-based diagnostics, challenges exist which must be solved for widespread commercial use. Not listed in order of importance, some of these challenges are disclosed herein.

One of the major challenges which must be dealt with in breath analysis, which will be addressed here, is that the ambient analytes in a patient's breath will be materially affected by where they live and even the environment of the office or testing area itself. A person living high in the Rocky Mountains will have a different ambient analyte profile than the individual who lives in midtown Manhattan. Not only must this be addressed for individual diagnosis but it also must be addressed so that comparative data from different geographical areas will have relevance and a similar baseline. That, as can be seen from this disclosure, is one of the key objectives of this application. The prior art makes it clear that potential innovators have struggled to develop functional analytical metrics to convert breath-based data into actionable diagnostics. Historically, the measurement instrumentation has been calibrated. As will be apparent from this disclosure, here, the patient is calibrated as well.

It is a further objective of this application to mitigate or remove contaminants that are naturally present in breath other than through the ambient air. Such contaminants that can skew breath samples include food aromas, activity in the nasal passages, mouthwashes, toothpaste, etc.

The present invention further seeks to address the challenges of breath-based diagnostics through novel compositions and/or methods, including compositions and methods that increase analyte levels in the breath.

It is of critical importance in understanding what follows, that in the past much importance has been placed on the calibration of the measuring instrument. Applicants will now place that same emphasis on calibrating the patient Applicants achieve this by the initial "wash out" composition and method described herein.

Additionally, applicants teach the amplification of the analyte through the use of an Amplification Agent, as described therein and also the possible use of a bronchodilator and also the collection of the post patient calibrated exhaled breaths in a container in order to maximize amounts of analytes even further.

In the "wash-out," the lungs are cleansed using a predetermined gas composition, e.g., a prepared gas composition, such as but not limited to, "bone dry calibration gas" as commonly used to calibrate instrumentation. This "wash-out" method replaces the existing air in the lungs with a controlled, clean breath composition that comprises a predefined blank slate against which to measure analytes regardless of the ambient air to which the patient has been subjected. Thus, the "wash out" process eliminates contaminants from the local atmosphere as well as most local contaminants otherwise present in the body. It is administered through the mouth and/or the nose, and even a tracheostomy tube in some cases. Thus a baseline is created wherein local contaminants are minimized and all patients start the testing at the same baseline regardless of where they live or where they are tested.

The predetermined gas composition is not limited but is something other than the ambient air in the location or room in which the subject's breath will be collected. In one preferred aspect of the invention, the predetermined gas composition is purified or filtered air. What is important here is the universality of the gas composition used so that the tests do not include contaminants and have universality of location relevancy.

One example of the predetermined gas composition or "wash out" gas is the gas produced by companies like Air Gas Corp. in Fort Lauderdale, Fla. The gas is known as "bone dry calibration air gas". It is pure to 5 digits unlike normal air gas supplies to hospitals, etc. Hospital air gas is 99.9% pure. Calibrating air gas is 99.99999% pure of known contaminants and is dry because all humidity is removed.

It is important to note that while dry calibration air gas is normally used for instrument calibration, applicants now teach its use for purposes of patient calibration—a novel application. While purity is important, the universality of the gas administered is also of importance. If one does not use "bone dry calibration gas" then it is preferable to use some other composition that has been determined and purified so that the test results are comparatively relevant.

It may be desirable to manipulate the content of the "wash out" gas in order to control the respiratory cycle. For example, $CO_2$ content is commonly understood to control the respiratory cycle; $O_2$ level and other constituents can have an effect. The point is that the "wash out" gas composition can be designed to normalize and/or optimize respiratory time cycles in connection with breath diagnostics. This is an important insight, because the rate of breathing is understood to have an effect on the levels of some analytes in the breath (see, e.g., U.S. Pat. No. 5,971,937, the entire contents of that patent being incorporated by reference herein).

"Wash out" gas may further include a bronchodilator. A bronchodilator is a substance that dilates the bronchi and bronchioles, decreasing resistance in the respiratory airway and increasing airflow to the lungs and more importantly maximizing the effect of the alveolar air/blood interface. A short acting bronchiodilator is the preferred embodiment (for example, and without limitation, β2-agonists and/or anticholinergics). Bronchodilators also can serve to augment alveolar transit through the effect of Bernoulli's Law, even if it is minimal.

As shown in Examples A and B, the bronchodilator, by maximizing the effective air exchange, will facilitate faster and more complete replacement of the air in the lungs with the "wash-out" composition and in the test phase, also maximize the amount of analyte in the breath through maximizing the blood/breath interface. Breath wash out serves an important function—to fully normalize patient-to-patient results by eliminating contamination. This allows for the comparison of data from multi centers across the world by nulling out the local contaminants and by establishing those metabolites that in fact are originating from the blood and not a local contaminant.

Preferably the wash-out is substantially completed within 350 seconds, more preferably within 300 seconds and most preferably within 250 seconds. Wash-out times are explored in Example A below. Wash-out times are explored in Example A below and, of course, bear a relationship to body size.

In the preferred embodiment, this same bone dry calibration air is continued into the diagnostic phase. In essence one does not return to ambient until the test is over.

It may be desirable to manipulate the humidity of the "wash out" gas to avoid desiccation or discomfort, although in this short time interval this is not so likely to apply.

Moreover, the present invention teaches the use of agents that enhance the concentration of the desired analyte—herein called "amplification agents". Such agents include the reverse use of "penetration enhancers," also known as "permeation enhancers" and would be applied to the wash-out and/or test phase, just as for the bronchodilator.

Such agents are typically used in drug delivery in enhance drug ENTRANCE absorption (or "penetration") across a human membrane—typically the skin, buccal mucosa, or vaginal mucosa and such agents are typically understood to work by disrupting the membrane structure and thereby facilitating transport across the membrane. Here the penetration agents' disruption of the membrane structure serves to enhance the EXIT transfer of the desired analyte FROM the blood to the alveolar interface. Applicants are aware of no prior art where penetration enhancers are employed in the diagnostic context to enhance EXIT TRANSIT of the analyte to better allow for measurement—i.e, as an Amplification Agent.

The Amplification Agent may include but is not limited to polyethylene glycol (PEG), diethylene glycol monoethyl ether (Transcutol), 23-lauryl ether, aprotinin, azone, benzalkom in chloride, cetylperidium chloride, cetylmethylammonium bromide, dextran sulfate, lauric acid, lauric acid/propylene glycol, lysophosphatilcholine, menthol, methoxysalicylate, oleic acid, phosphaidylcholine, polyoxyethylene, polysorbate 80, sodium EDTA, sodium glycholated, sodium glycodeoxycholate, sodium lauryl sulfate, sodium salicylate, sodium taurocholate, sodium taurodeoxycholate, sulfoxides, and various alkyl glycosides or, as described in U.S. Patent Application Publication No. 2006/0257463, bile salts, such as sodium deoxycholate, sodium glycodeoxycholate, sodium taurocholate and sodium glycocholate, surfactants such as sodium lauryl sulfate, polysorbate 80, laureth-9, benzalkonium chloride, cetylpyridinium chloride and polyoxyethylene monoalkyl ethers such as the BRIJ® and MYRJ® series, benzoic acids, such as sodium salicylate and methoxy salicylate, fatty acids, such as lauric acid, oleic acid, undecanoic acid and methyl oleate, fatty alcohols, such as octanol and nonanol, laurocapram, the polyols, propylene glycol and glycerin, cyclodextrins, the sulfoxides, such as dimethyl sulfoxide and dodecyl methyl sulfoxide, the terpenes, such as menthol, thymol and limonene, urea, chitosan and other natural and synthetic polymers. Preferably, the Amplitude Enhancer is a polyol, e.g., polyethylene glycol (PEG), glycerin, maltitol, sorbitol etc. or diethylene glycol monoethyl ether (Transcutol).

It will be understood that amplification agents may also be used in connection with other, non-breath diagnostics. For example, an amplification agent may be applied to the skin to enhance topical measurement of an analyte for diagnostic purposes (by enhancing transit or exit of the analyte from the blood through the skin). Amplification agents can also be used in bodily cavities for similar diagnostic use.

In some cases the use of altered air currents might be used to facilitate deep alveolar air movement, such as but not limited to ultrasonics. These may be employed in the washout and/or diagnostic exhalation phase. In addition, it may be desirous to induce mild coughing during washout and/or the test phases. These may be involve patient directed coughing or agent induced coughing. Furthermore closed circuit inhalation/exhalation may be employed in the testing phase for the purpose of augmenting the concentration of certain analytes. This may be in place of the closed container exhalations and/or in conjunction with same.

Modified pressure (greater or less than one bar) may be utilized for speed or thoroughness in the wash-out. Additionally, reduced pressure or suction may be desirable to enhance exit transit of the desired analyte into the breath.

Analytes in the breath may be of disease markers but also could be analytes of therapeutic drugs or their metabolites and/or adverse side effects of therapeutic drugs. These are either through direct markers or indirect or proxy metabolic markers and might also be used to ascertain if certain therapeutic levels were being reached. The analyte may be any other analyte, testing for which is useful, e.g., an analyte of an illegal substance or a controlled substance, e.g., alcohol.

In addition, by the use of a closed container to capture the post washout diagnostic exhaled purified calibration gas, it is allowed for a gathering and concentrating and amount of the analyte one is seeking. The closed container can be expandable. This is akin to blowing in a balloon or a closed container in which the amount of the analyte, through a one way valve, is accentuated.

At the completion of the washout phase, breath collection begins immediately so that no ambient contamination can alter the analyte content results. Thus, before the subject inhales anything other than the predetermined washout gas, the subject exhales to an analyzer or to a container for collecting the subject's breath.

Example A

Simulated Lung Washout Experiments

The following experiments were carried out in order to determine the average time to washout a subject's lungs.

In the washout experiments, the setup included a large transparent plastic jar having a volume of 4.7 liters (corresponding to adult lung volume), shown schematically in FIG. 1. The jar 1 was placed upside down on a flat surface and sealed on a gasket. Through the flat surface, there were four connections to the jar. One was for introducing a smoke contaminant to the "lung" (with a shut-off valve 2), one was for introducing filtered fresh air (with a one-way valve 3), one was for removing the smoke contaminant (with a one-way valve 4) and the last connector to the lung was for our smoke sensor 5. The smoke sensor 5 was located inside the "lung" 1 so that we could measure the amount of smoke initially introduced and then diluted/removed with each breathe.

The smoke sensor 5 used for these experiments gave a voltage output that allowed measurement of the level of the smoke throughout the washout tests. The sensor 5 was located inside the "lung" 1 and the electrical connections to the data logger were directly transferred to the computer. This enabled automatic collection of the level of the smoke contaminant in the "lung" 1 before the smoke was added, during the smoke addition, and throughout the washout using 15 room air breathes per minute at 0.5 liters in and out.

To run the wash out experiments, the following steps were used:

1. Make sure the experimental set up is at an equilibrium before the start of the test.
2. Start recording the smoke sensor data before the smoke is introduced (A in FIG. 2). This gives a "baseline" measurement of the room air.
3. Introduce a quick "shot" of cigarette smoke to the "lung". The smoke could be seen entering the transparent container (B in FIG. 2).
4. When the smoke is introduced to the "lung", all the connectors are closed off. Nothing can get in or out.
5. Keep recording the smoke sensor data until the smoke concentration in the "lung" reached a steady state (C in FIG. 2). In other words, wait until the smoke throughout the lung was uniform.
6. Start the timer and start manually breathing in and out at 0.5 liters for both the inhalation and exhalation (D in FIG. 2). The breathe in was filtered room air.
7. Keep recording the data from the smoke sensor until the same baseline in the "lung" before the smoke was introduced is reached (E in FIG. 2). Then the experiment was finished.

For each test the equipment was disassembled and washed out all of the surfaces so that another test can be started.

FIG. 2 conceptually illustrates these steps and results "A" through "E" in FIG. 2 refer to the steps explained above.

Figure 3:
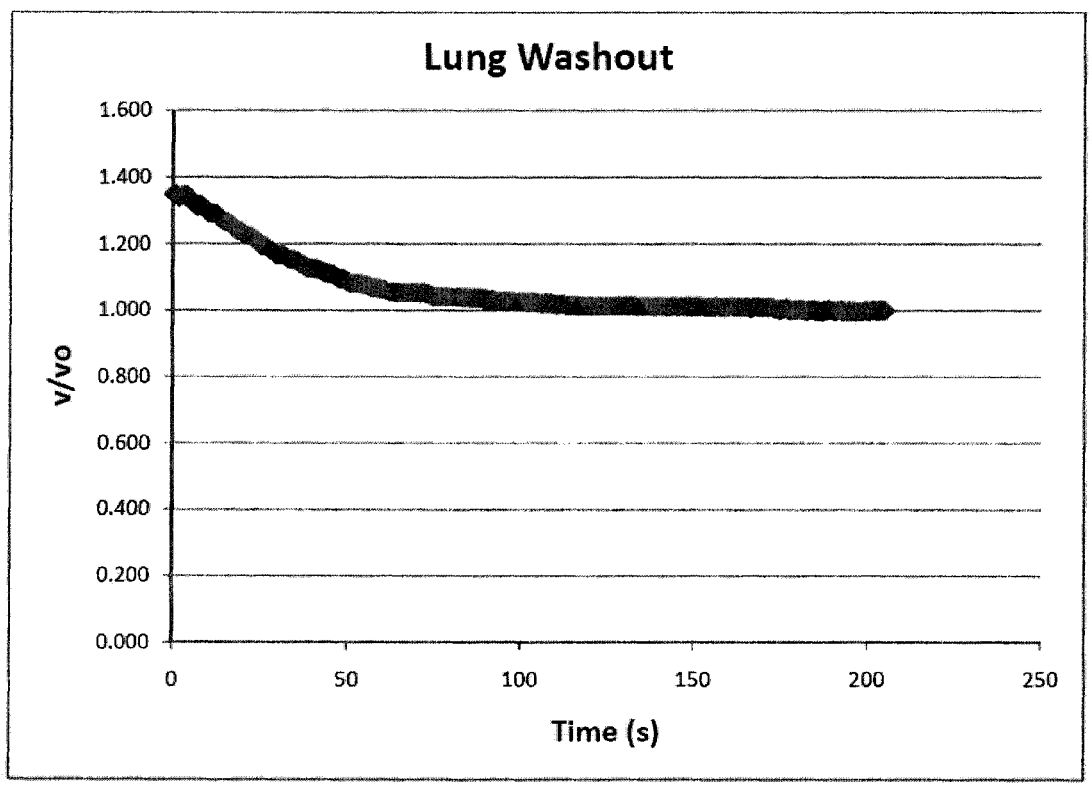
Figure 4:
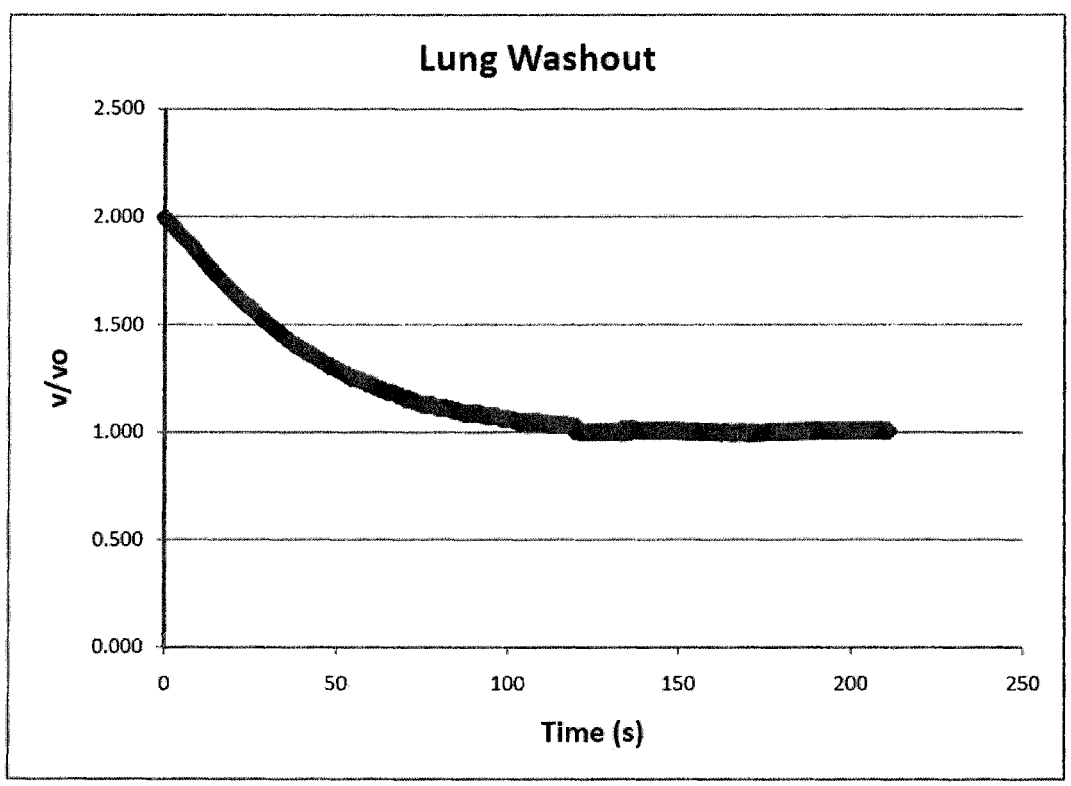

FIGS. 3 and 4 are representative of results for the washout experiments. Here a single shot of cigarette smoke (approximately 0.5 liters) was introduced to the transparent polycarbonate jar, the smoke concentration allowed to equilibrate through the vessel, and manual simulation of breathing begun with individual pumps for inhalation and exhalation. Each pump stroke was set to deliver/withdraw 0.5 liter volume. An in-line air hepa filter was added to the clean air inlet and the exhaust smoke was separately disposed of through an external exhaust vent.

The MQ-2 smoke detector that was used in these experiments covers the range of 300 to 10,000 ppm in a voltage range of 0-5 volts. Data is reported in terms of the actual voltage reading or variant thereof.

FIG. 4 shows the results at the end of the equilibrium period and the start of the washout. Smoke concentration is shown as $v/v_O$, the ratio of the smoke sensor voltage to the starting baseline voltage. The data is presented in terms of the sensor voltage which is proportional to the smoke concentration. When $v/v_O=1$ is known that the washout is complete within the sensor measurement capability. The parameter, $v_O$, is the initial baseline sensor voltage reading, while "v" is the sensor reading as a function of experimental time during the course of the measurement.

Figure 5:
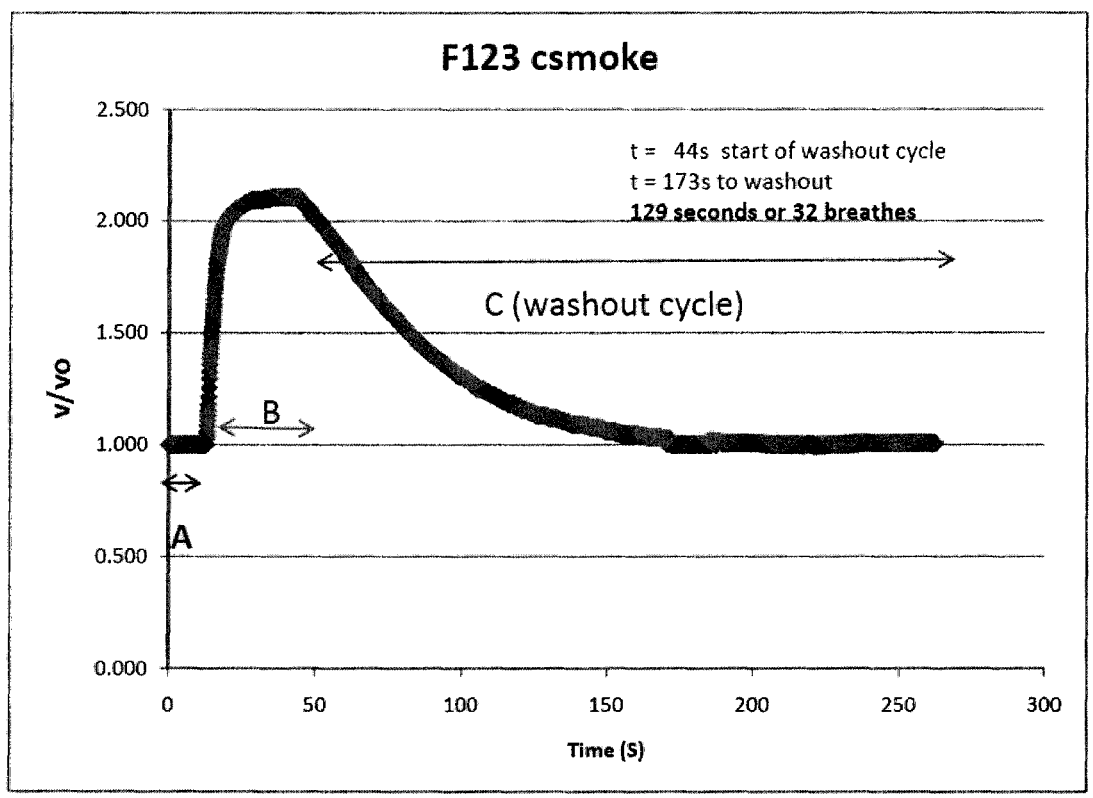

FIG. 5 shows the complete experimental measurement cycle, showing the initial equilibrium smoke sensor value (A), the smoke introduction/equilibration phase (B), and washout (C).

Figure 6:
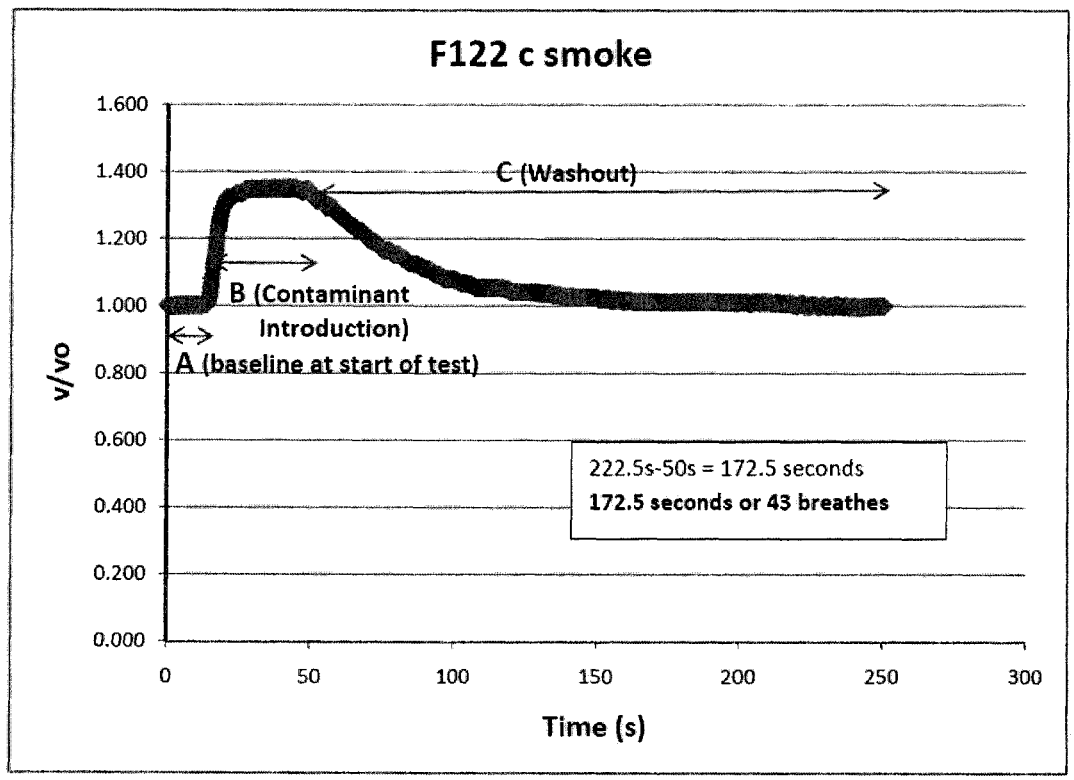

Another example of the total experimental measurement is shown in FIG. 6.

Figure 7:
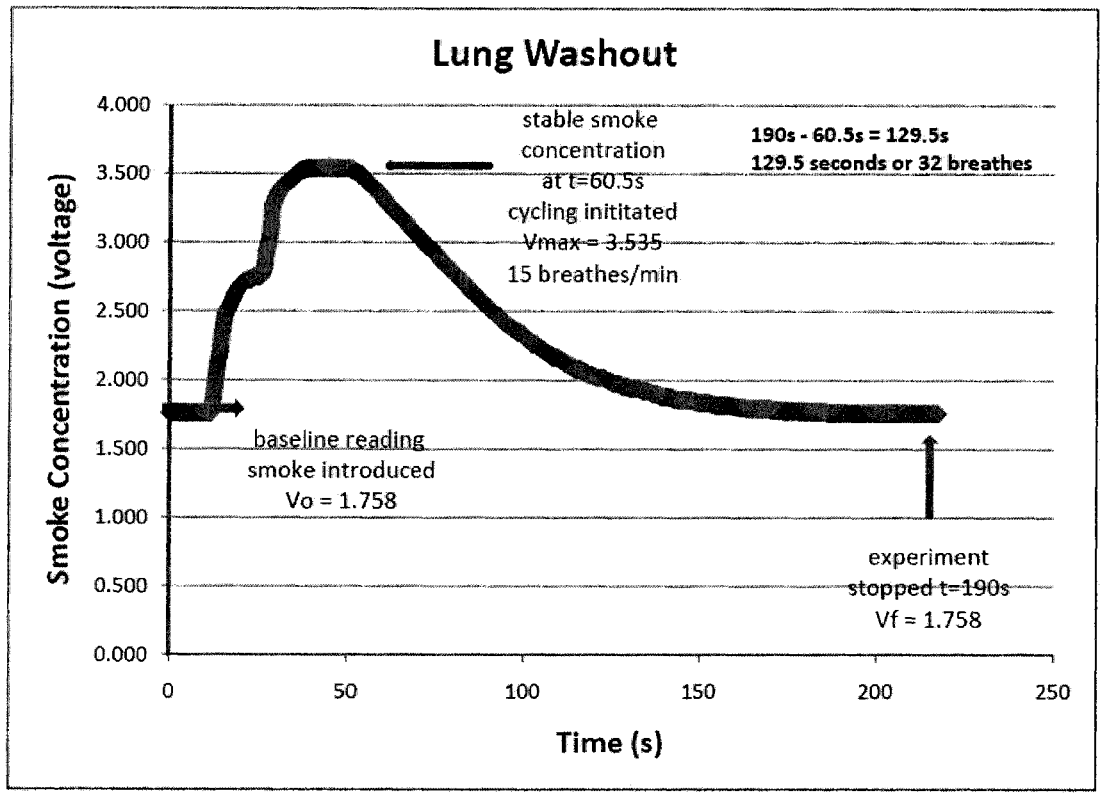

FIG. 7 shows the results of one additional measurement for which data acquisition was used. In this experimental of lung washout, 129.5s was required or 32 breaths.

Using the sensor in all of our measurements, the average washout time is 142 seconds or 36 breathes assuming 15 breathes/minute, n=5.

This suggests a wash-out interval of 36 breaths or 142 seconds for a 4.2 liter lung. Longer times can be extrapolated for an adult male lung of approximately six liters in capacity.

Example B

The data shown in Example B follows the same principles as Example A with the exception that Example B only measured how long it took to introduce the smoke contaminant through the 10 mil and 30 mil holes with and without gauze, without any washout taking place. By comparison with the results shown in FIG. 2, Example B only measured "A" through "C". In this test the smaller and larger hole sizes were used a proxies for a bronchodilator, the number of openings are proxy for the bronchodilator/guaze effect and the gauze was used as a proxy for the presence or absence of a penetration enhancer.

The test results were developed using experimental 10 and 30 mil diffusers (with 1, 3 and 9 holes), with and without gauze. To assist in the interpretation of these results, two tables follow.

These diffuser measurements started with a clean inverted plastic jar equipped with the smoke sensor. The sensor has only room quality air at the start of the test. While the smoke sensor recorded the ambient room temperature conditions in the plastic "lung," approximately 0.5 liters of smoke were introduced via an inflated balloon. The smoke passes through the diffuser before entering the "lung." Experiments are run with and without gauze in the 1, 3 and 9 hole diffusers.

As part of the experiments, the smoke concentration in the "lung" was recorded as the smoke is introduced to the diffuser and the smoke concentration in the plastic lung was continued to be recorded until an equilibrium value was reached ($t_{eq}$). Because data was continuously being collected during the experiments, the final test results are tabulated in terms of $t_{eq}$, which is the total time duration from the start of the test to the end. The results are also tabulated in terms of how long it took to reach 50% of the total equilibration time, $t_{50}\%$.

A typical data record from the experiments is shown in FIG. 3. This shows the increasing smoke concentration in the lung as it is being passed through the diffuser from the smoke filled balloon for a single 0.010" diffuser hole without gauze.

Here, the progressive increase in smoke concentration in the "lung" is being shown as the smoke passes through the diffuser into the lung. The smoke concentration reaches a maximum at approximately 770s and this ends our test. We also looked at the time to reach 50% of the final smoke contamination. This occurs in less than 100 seconds. We used both of these time values to compare our results for each of the diffuser experiments. Tables 1 and 2 summarize the experiments in terms of the final contaminant equilibration time for the 10 and 30 mil diffusers, with and without gauze.

In these experiments, the 10 and 30 ml openings are a proxy for the role of a broncho dilating effect, and the 1, 3, and 9 holes are a proxy as well for a bronchodilating/guaze effect and the guaze is a proxy for the presence or absence of a tissue transport enhancing agent.

TABLE 1

| Size | Holes | Time (eq) |
|---|---|---|
| (10 mil without gauze) | | |
| 10 mils | 1 | 774.4 |
| 10 mils | 3 | 632.0 |
| 10 mils | 9 | 104.5 |
| (10 mil with gauze) | | |
| 10 mils | 1 | 3500 |

TABLE 2

| Size | Holes | Time (eq) |
|---|---|---|
| (30 mil without gauze) | | |
| 30 mil | 1 | 115.6 |
| 30 mil | 3 | 31.5 |
| 30 mil | 9 | 16.3 |
| (30 mil with gauze) | | |
| 30 mil | 1 | 112 |
| 30 mil | 3 | 37.6 |
| 30 mil | 9 | 30.8 |

The 10 mil single hole With and Without gauze was tested, and a very large difference in results was found. For the 10 mil diffusion, single hole with gauze, the time to reach equilibrium contaminant concentration is nearly one hour, at 3500 seconds. This is in sharp contrast to the 750 seconds needed for the 10 mil diffusion, single hole, without gauze.

The differences are not as pronounced for the 30 mil results, with and without gauze. Without gauze, the time to each a steady smoke concentration decreases with increasing number of holes as applicants would expect.

Tables 3 through 4 list all of the experimental times recorded for smoke to pass through the 10 and 30 mil diffusers with 1, 3 or 9 holes, with and without gauze. Here, the individual results for each measurement as well as the average values can be seen.

TABLE 3

10 mil without gauze: Left Column
10 mil with gauze: Right Column

| Size | Holes | $Time_{50}$ | $Time_e$ | size | holes | $Time_{50}$ | $Time_e$ |
|---|---|---|---|---|---|---|---|
| 0.010" | 1 | 90.6 | 794.1 | 0.010" | 1 | 500 | ≅3500 |
| | | 83.2 | 754.6 | | | | |
| average | | 86.9 | 774.35 | | | | |
| 0.010" | 3 | 43.5 | 326.0 | | | | |
| | | 29.2 | 99.2 | | | | |
| | | 12.7 | 109.7 | | | | |
| average | | 21.0 | 104.5 | | | | |

TABLE 4

30 mil without gauze: Left Column
30 mil with gauze: Right Column

| | | | | | | | |
|---|---|---|---|---|---|---|---|
| 0.030" | 1 | 13.8 | 109.5 | 0.030" | 1 | 23.4 | 108.9 |
| | | 12.6 | 121.7 | | | 25.9 | 115.0 |
| average | | 13.2 | 115.6 | average | | 24.7 | 112.0 |
| 0.030" | 3 | 2.8 | 28.2 | 0.030" | 3 | 6.3 | 33.4 |
| | | 4.3 | 37.3 | | | 7.9 | 41.7 |
| | | 5.2 | 29.1 | | | | |
| average | | 4.1 | 31.5 | average | | 7.1 | 37.6 |
| 0.030" | 9 | 3.3 | 16.1 | 0.030" | 9 | 4.4 | 27.0 |
| | | 4.3 | 18.1 | | | 5.0 | 34.6 |
| | | 3.4 | 14.8 | | | | |
| average | | 3.7 | 16.3 | average | | 4.7 | 30.8 |

In comparing the results of the 3 mil diffusers with and without gauze, the biggest difference appears to be in the time to reach 50% of the final value. The influence of the gauze in these experiments gives rise to a slower initial diffusion rate. This is most apparent in the 30 mil single hole results with an average time to reach 50% being 13.2 seconds for the diffuser without gauze and 24.7 with gauze. In terms of the final equilibration times, the 30 mil 9 hole diffusers from a total equilibration time difference of 16.3 seconds without gauze vs. 30.8 seconds with gauze.

Perhaps the best example of the initial "delay" in the contaminant concentration equilibration in the "lung" can be shown in FIG. 4 for the 30 mil 3 hole diffuser with and without gauze.

There appears to be an initial induction time or delay for the two measurements completed with gauze.

The experimental setup and the diffusers were washed and cleaned before each test. The 0.010" and 0.030" diffusers were easily clogged and/or fouled during each test. This was especially noticeable for 0.010" holes where we could visibly see strands of dirt collect at the exit of the holes to the "lung."

In Example B, the different hole sizes were to represent the use of a broncho dilator and the increased speed and amount of analyte passing into the lung from the blood vessels of the alveolus. The addition of gauze was to represent the effect of adding an amplification agent in the non gauze (compared to the non enhanced gauze results).

The results demonstrate that the best transport occurs with the surface area (number of holes, simulating bronchodilation) without guaze (amplification agent present).

The invention claimed is:

1. A method of avoiding ambient analytes which would skew an analyte result in a breath analysis method and of calibrating subject of the breath analysis comprising, immediately before a breath analysis method or collection of breath for a breath analysis method, administering to the subject a predetermined purified and standardized gas composition, the predetermined purified and standardized gas composition being something other than ambient air from the area in which the breath of the subject will be collected, being free of an ambient analyte which would skew an analyte result in a breath analysis method and having a universality of composition regardless of the area in which the breath of the subject will be collected and being at least 99.99999% pure of known contaminants.

2. The method of claim 1, further comprising collecting a breath sample from the subject into a closed container under reduced pressure to enhance exit transit of the desired analyte into the breath.

* * * * *